(12) United States Patent
Nissels

(10) Patent No.: US 7,060,054 B2
(45) Date of Patent: Jun. 13, 2006

(54) SUCTION PIECE FOR OR ON A DEVICE ADMINISTERING AN INJECTABLE PRODUCT

(75) Inventor: Robert Nissels, Fountainemelon (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 10/053,270

(22) Filed: Jan. 17, 2002

(65) Prior Publication Data
US 2002/0128600 A1 Sep. 12, 2002

(30) Foreign Application Priority Data
Jan. 17, 2001 (DE) .................. 101 01 932

(51) Int. Cl.
*A61M 5/315* (2006.01)
(52) U.S. Cl. ........................ 604/218; 604/131
(58) Field of Classification Search ................ 604/218, 604/115, 186, 187, 208, 264, 272, 131, 140, 604/151
See application file for complete search history.

(56) References Cited

U.S. PATENT DOCUMENTS

| 4,284,077 A | * | 8/1981 | Wagner ...................... 604/115 |
| 5,782,871 A | | 7/1998 | Fujiwara et al. ............ 604/313 |
| 6,280,421 B1 | | 8/2001 | Kirchhofer et al. ......... 604/218 |

FOREIGN PATENT DOCUMENTS

| DE | 25 51 991 A1 | 7/1976 |
| DE | 37 13846 A1 | 4/1988 |
| DE | 197 08 256 A1 | 9/1997 |
| DE | 37 08 031 A1 | 11/1997 |
| DE | 198 22 031 A1 | 11/1999 |

* cited by examiner

Primary Examiner—Kevin C. Sirmons
(74) Attorney, Agent, or Firm—Dorsey & Whitney LLP

(57) ABSTRACT

A suction piece for a device for administering an injectable product, the suction piece including a suction chamber having a chamber opening rim via which the suction piece may be placed on a tissue, a connection part in order to produce a mechanical connection to the device, a first passage extending through the connection part into the suction chamber in order to produce a fluid connection between the suction chamber and a product reservoir of the device, wherein the pressure in the suction chamber may be reduced when the chamber opening rim is placed on the tissue in order to apply suction to the tissue.

6 Claims, 6 Drawing Sheets

SUCTION PIECE FOR OR ON A DEVICE ADMINISTERING AN INJECTABLE PRODUCT

PRIORITY CLAIM

The above-identified patent application claims priority to German Patent Application No. 101 01 932.7, filed on Jan. 17, 2001.

BACKGROUND OF THE INVENTION

1. Technical Field

The invention relates to administering injectable products, preferably subcutaneously administering to human beings.

2. Description of the Related Art

The administering device in accordance with the invention is preferably an injection device, for example an injection pen or a simple syringe. In principle, however, the invention as an infusion device can also be advantageously used. Preferred injection or infusion devices are portable devices, such as are known for example in insulin treatment or also in hormone therapy. The invention is not, however, restricted to the preferred application in portable injection and infusion devices, but may also be used in stationary administering devices.

When administering medicinal liquids by way of an injection or infusion into or under the skin, an as fast a dispersal and dissipation to the effective site as possible is sought. If the liquid is administered by means of an injection needle to penetrate through the skin or at least through the upper layers of the skin, then perforation should be as painless as possible.

SUMMARY OF THE INVENTION

It is therefore an object of the invention to enable the administered product to dissipate fast from the site of being administered to the effect site and/or to be administered as painlessly as possible.

The invention has as its subject a device for administering an injectable product using a suction chamber and furthermore a suction piece which can be connected to a device for administering an injectable product and which forms the suction chamber.

The device for administering the product includes a casing with a receptacle for the product and a dispensing means with an opening through which the product may be administered into a tissue, preferably into or under the skin. The receptacle of the casing can directly form a product reservoir. Preferably, however, a product reservoir is formed by a container filled with the product, particularly preferably an ampoule, which may be inserted into the receptacle of the casing. The product can be administered from the reservoir through the dispensing means. The dispensing means can be an injection needle or also a pressure injector, through which the product can be introduced into the tissue without the dispensing means having direct contact with the surface of the tissue.

The dispensing means opens into the suction chamber via its opening. The suction chamber comprises an exposed chamber opening rim which is placed onto the tissue when administering. Once it has been placed on the tissue, the suction chamber and the tissue form a closed hollow space which is sufficiently sealed to reduce the pressure in the hollow space formed in this way. By generating a partial vacuum, tissue within the placed opening rim of the suction chamber is suctioned into the suction chamber. The suctioned tissue forms a bulge of tissue or fold of skin in the suction chamber, into which the product is delivered when administering by means of the dispensing means.

By forming the bulge of tissue, blood circulation in the area of the administering site is improved. The improved blood circulation ensures that the administered product is transported away faster. The product therefore exhibits its effect faster than without forming the bulge. Furthermore, the pain associated with perforating the skin is reduced, since the skin is tensed by the suction and thus the force of pressure required to perforate the skin is reduced.

Lastly, as a third advantage, administering is simplified. If, for example, a diabetic has hitherto formed a fold of skin for injecting the injection needle at the desired injection site using two fingers, then he has always needed both hands in order to form the fold of skin and introduce an injection needle into the fold of skin. Due to the suction of the tissue at the site of product delivery in accordance with the invention, the user now only needs one hand to administer the product, if for example the tissue is suctioned beyond the tip of the needle and the injection needle is thus introduced into the tissue. In the case of automatic suction by means of a pump, only a simple hand movement is required to trigger the pump action, which can be performed by the same hand as is holding the device.

In preferred embodiments, the suction chamber is permanently connected to a pump or can be connected for use. The term pump is to be understood as any means suitable for generating a partial vacuum in the suction chamber. It is preferably a manually operable pump. A passage is formed in a wall of the suction chamber for connection to an external pump. The partial vacuum for suctioning the tissue is admittedly preferably generated by a pump arranged externally, i.e. outside the suction chamber, however the invention is not restricted to this. The suction chamber can thus be equipped, for example, with a flexible chamber wall, such that the partial vacuum is generated by enlarging the volume of the suction chamber. The suction chamber can in this case be formed as a flexible sucker, on which a suction force is exerted once the device has been placed on the surface of the tissue. Through the suction, the volume of the flexible suction chamber is enlarged in the suction direction and/or perpendicularly to the suction direction. When the volume is enlarged in the suction direction, a flexible suction chamber is preferably used in combination with an administering device formed as an auto-injector, when an injection needle is used as an infusing part.

The suction chamber can be an integral component of the casing of the administering device. In particular, it can be injection-moulded from a single plastic material in a single piece together with the casing, or it can be injection-moulded from a different plastic material to the casing, in particular a softer plastic material, connected to the device in a material bond, in particular in two pieces.

In alternative, particularly preferred exemplary embodiments, the suction chamber is formed by means of a separate suction piece which comprises a connecting part for connecting to an administering device. The connection to an administering device can be formed non-detachable after manufacture or preferably detachable. It can be made non-detachable by a positive lock between the administering device and the suction piece, for example by means of a locking connection. A detachable connection is preferably realised by means of a screw connection, a bayonet lock or a detachable locking connection which can also be combined with the other types of connection. In principle, connecting a separately produced suction piece in a material bond may also be considered.

If an external pump is used to evacuate the suction chamber, then the pump is either an integral component of the administering device of a separate suction piece, in preferred exemplary embodiments. Since the pump can however in principle be formed in any way, the use of a separate pump which if necessary must be connected by the user can also not be ruled out.

In preferred embodiments, a bilaterally acting pump is used. A pressure increase on a pressure side of the pump, necessarily associated with the suction work, is usefully used for delivering the product. If the product reservoir is formed by an ampoule comprising a piston accommodated in it, the pressure side of the pump can be connected to the rear side of the piston and can move the piston in the ampoule, such that the product is forced out of the ampoule by the movement of the piston and is delivered by the dispensing means. If the administering device is formed by an auto-injection device, then the pump pressure of the pressure side of the pump can act on a carrier means for the ampoule—conventional in auto-injectors—and advance said carrier means in the casing of the device toward the tissue, in order to inject the injection needle into the tissue. The pressure increase associated with the suction work can also effect the delivery and the injection of an injection needle, in combination.

BRIEF DESCRIPTION OF THE DRAWINGS

Preferred embodiments of the invention will now be described by way of exemplary embodiments. The features disclosed in the exemplary embodiments, each individually and in every disclosed combination, advantageously develop the subjects of the claims.

DETAILED DESCRIPTION

Figure 1:
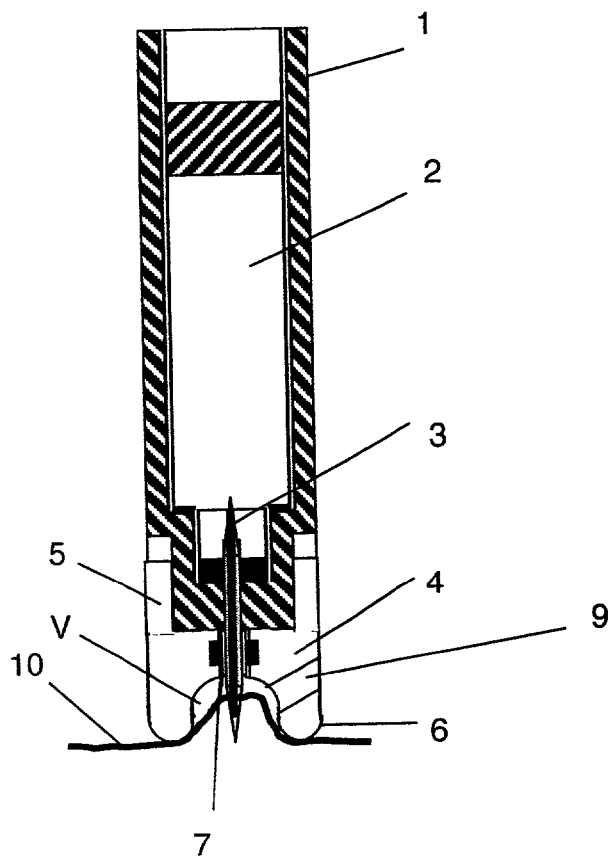
FIG. 1 depicts a suction piece detachably connected to an administering device.

FIG. 1 shows a longitudinal section of a device for administering an injectable product, for example insulin, while the product is being administered. The device is formed by an injection pen, such as is known to the person skilled in the art. Of the device, only a casing 1, a product reservoir 2 and a dispensing means 3 are shown. The product reservoir 2 is formed by a conventional ampoule comprising a piston accommodated in it. The ampoule is inserted in a receptacle of the casing 1 in a known way. The dispensing means is formed as a conventional injection needle which is connected to the product reservoir 2 in a way known in its own right, and which protrudes straight from the casing 1 at a proximal end.

A suction piece 4 is detachably screwed on at the proximal end of the casing 1. The suction piece 4, which may be repeatedly connected to the casing 1, is shown individually in FIG. 2 detached from the administering device.

The suction piece 4 is sleeve-shaped as one piece, and forms a connection part 5 at an end facing the administering device. At a proximal end facing away from the administering device, the suction piece 4 forms a suction chamber V comprising a hollow space generally defined by means of a wall 6. The proximal end of the suction piece 4 includes a chamber opening rim 6' extending generally circumferentially around the opening into the suction chamber V. When the device is placed on the surface of the tissue ,i.e., when the rim 6' is placed against the skin, the tissue surface and wall 6 fully define the suction chamber V. The connection part 5 and the wall 6 of the suction chamber V are separated from each other by a partition extending radially to the longitudinal axis of the suction piece 4. A passage 7 extends through the partition, co-axially to the central longitudinal axis. The passage 7 is sealed air-tight by a seal 8 arranged in the passage, a septum. The partition together with the seal 8 forms an air-tight separating area between the distally open connection part 5 and the proximally open suction chamber V. Corresponding to preferred example embodiments, the suction piece 4 can be realised as an otherwise one-part plastic injection part by extrusion-coating the seal 8.

In order to connect the suction piece 4 to the administering device, the suction piece 4 together with the connection part 5 is screwed onto the proximal end of the device. In the course of screwing the suction piece 4 and the connection part 5 on, the injection needle 3 is pushed through the passage 7 and so penetrates through the seal 8. After the needle 3 has pierced the seal 8, the seal 8 surrounds the injection needle 3 air-tight.

Instead of in the passage 7, the seal 8 can also be arranged elsewhere, it must only be ensured that the passage 7 for the injection needle 3 or another dispensing means is sealed air-tight, for the purpose of evacuating the suction chamber V. This can, for example, also be achieved by arranging the seal between the proximal end of the casing 1 and the rear outer area of the suction piece 4, at which the passage 7 opens, or by sealing in the area of the screw connection between the casing 1 and the suction piece 4.

A passage 9 leads through the wall 6 of the suction chamber V, i.e. the passage 9 opens at one end in the suction chamber V, and at its other end on an outer surface area of the suction piece 4. The passage 9 serves to connect a pump for evacuating the suction chamber V.

To administer the product, the administering device is placed on the tissue 10 at the desired point of injection via the exposed chamber opening rim 6' of the suction piece 4. In this state, the suction chamber V is substantially sealed. A slight distance remains between the surface of the tissue and the tip of the injection needle 3. In this position, the suction chamber V is evacuated via the passage 9, i.e. a partial vacuum with respect to the surroundings is generated in the chamber V. Due to the partial vacuum, the tissue is suctioned into the suction chamber V toward the tip of the injection needle 3. A bulge of tissue is formed under the tip of the needle. In the preferred application, subcutaneous injection, the bulge of tissue is a fold of skin. With increasing evacuation, the bulge of tissue swells further up and is suctioned beyond the tip of the needle. In other words, the injection needle 3 penetrates into the bulge of tissue. This state is shown in FIG. 1. The product can now be delivered from the reservoir 2 through the injection needle 3 into the tissue 10.

Figure 2:
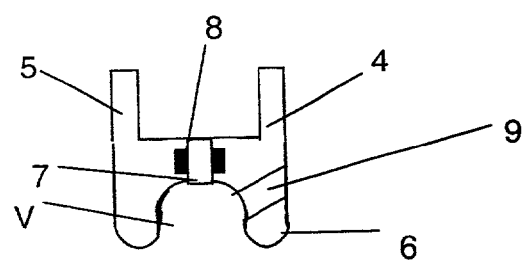
FIG. 2 depicts the suction piece from FIG. 1 in an individual representation.
Figure 3:
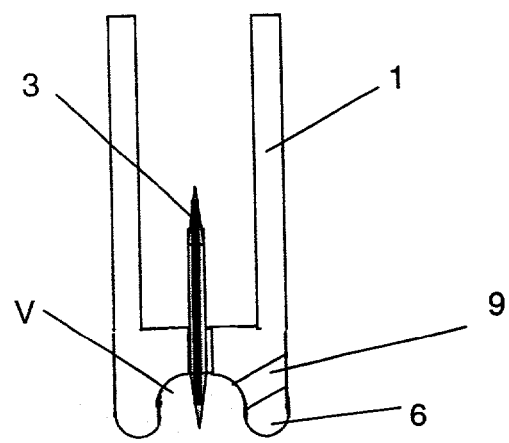
FIG. 3 depicts an administering device comprising an integrated suction chamber.

FIG. 3 shows the proximal end of an administering device comprising an integrated suction chamber V. As opposed to the exemplary embodiment in FIGS. 1 and 2, the chamber wall 6 together with the passage 9 is an integral component of the casing 1 of the device. In the exemplary embodiment of FIG. 3, the casing 1 and the chamber wall 6 are injection-moulded as one piece from a plastic material. The injection needle 3 is surrounded air-tight by the plastic material; it can, for example, be inserted into the injection mould during manufacture and extrusion-coated with the plastic material. In this way, a disposable syringe in particular can be manufactured. In the case of a reusable injection device comprising an integrated suction chamber V, a seal would again have to be provided in a passage for the injection needle 3 or another dispensing means, for example a high pressure injector, as in the exemplary embodiment in FIGS. 1 and 2.

Figure 4:
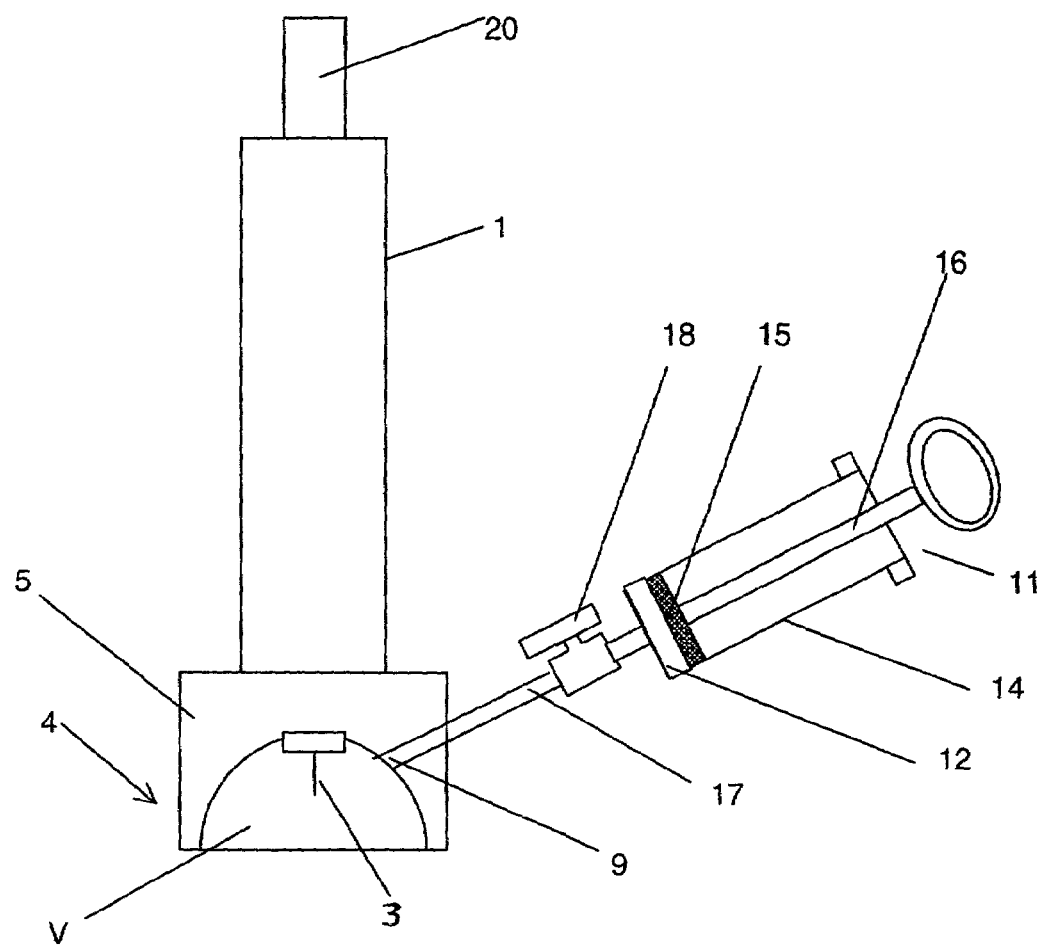
FIG. 4 depicts an administering device comprising a pump in a first embodiment.

FIG. 4 shows the device from FIGS. 1 and 2, further comprising a connected pump 11. The pump 11 is a piston pump comprising a piston 15 accommodated linearly moveably in a cylinder 14. A piston rod 16 projects from a rear side of the piston, said piston rod 16 leading Out of the cylinder 14 for manual operation of the pump 11. The suction side 12 of the pump 11 is connected to the passage 9 of the suction piece 4 via a connection line 17. A manually operable cut-off valve 18, with which the connection line 17 can be opened and closed, is arranged in the connection line 17.

To administer the product, the pump 11 is tensed in a first step, i.e. the piston 15 is retracted in the cylinder 14 and a partial vacuum is thus generated on the suction side 12 of the pump 11. The piston 15 is latched in this position. Then the rim 6' of the device is pressed against the tissue with slight pressure at the point of injection as already described. In the next step, the valve 18 is opened, such that instantaneous pressure equalization takes place between the suction side 12 of the pump 11 and the suction chamber V via the connection line 17 and the passage 9. Due to the partial vacuum momentarily resulting in the suction chamber V, the tissue is suctioned into the suction chamber V and so simultaneously tensed at its surface, together facilitating the penetration of the skin by the injection needle 3. The product is then delivered by activating a delivery means 20. Preferably, suctioning the tissue simultaneously strengthens blood circulation in the suctioned area of tissue and so accelerates the transporting of the delivered product away from the delivery site.

Figure 5:
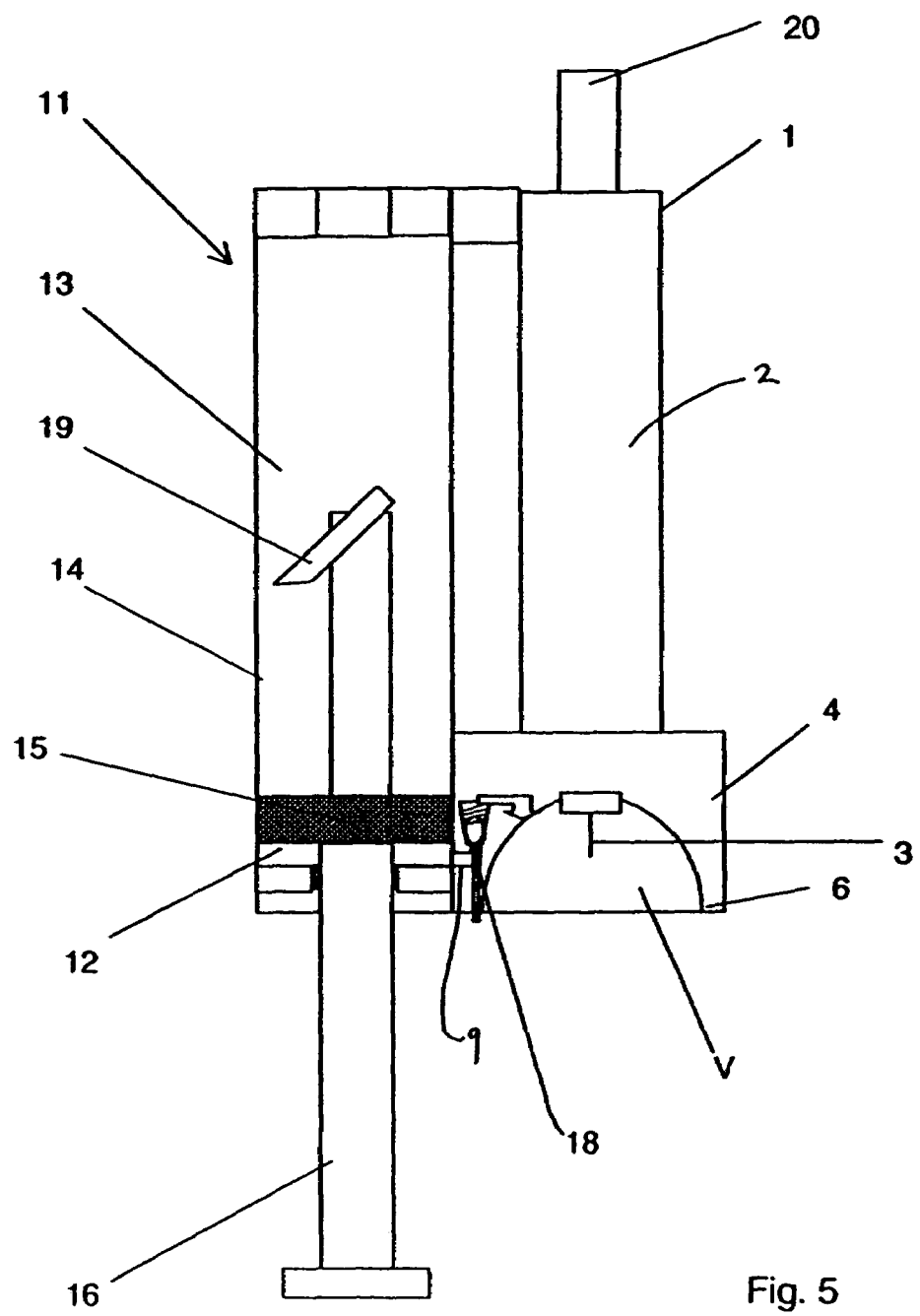
FIG. 5 depicts the administering device from FIG. 4 comprising a pump in a second embodiment, in a starting position.
Figure 6:
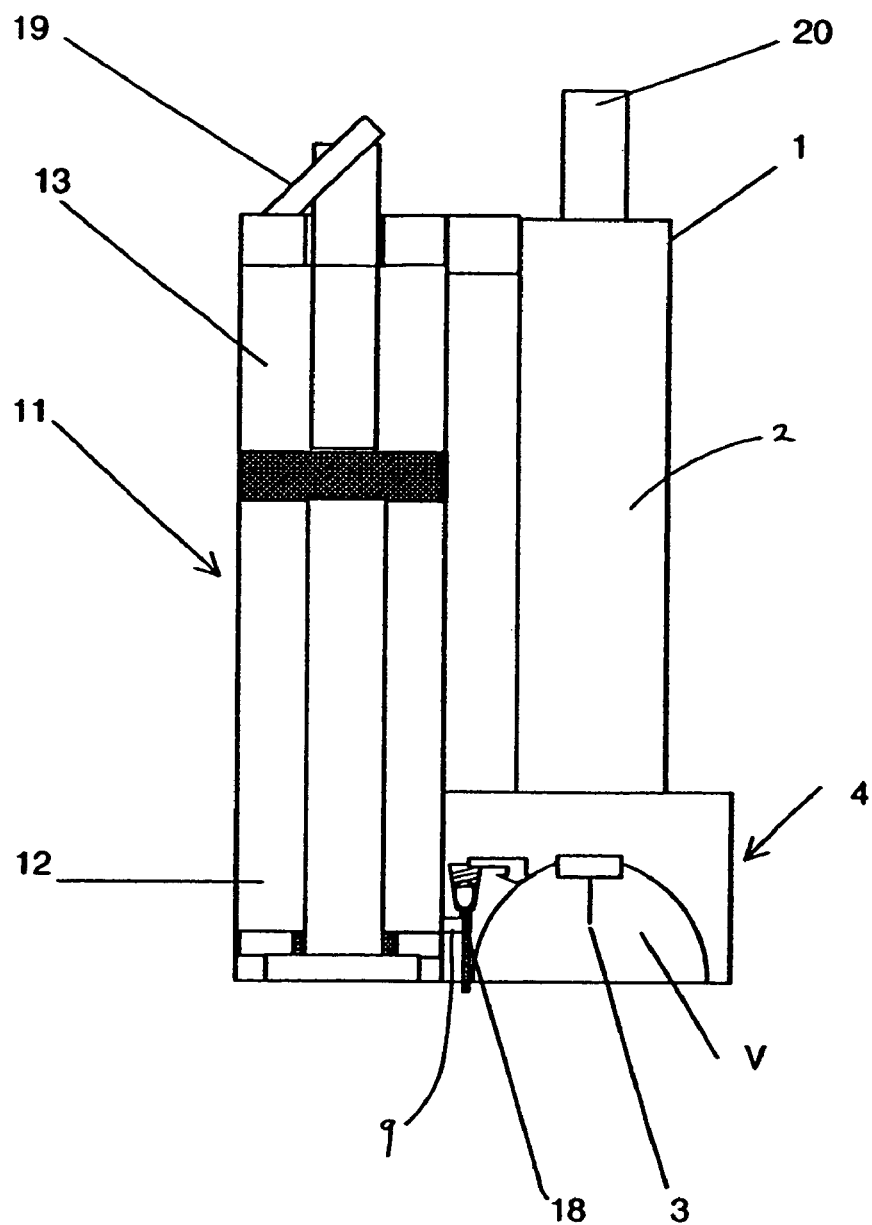
FIG. 6 depicts the administering device from FIG. 5 comprising the pump in an end position.

FIGS. 5 and 6 show the administering device from FIG. 4 comprising an alternative embodiment and arrangement for a pump 11. The pump in this exemplary embodiment is likewise formed by a piston pump comprising a cylinder 14 and a piston 15 accommodated linearly moveably in it. The cylinder 14 is fixed to the casing 1 of the device; it can also be an integral component of the casing 1. The longitudinal axis of the cylinder 14 runs parallel alongside the longitudinal axis of the administering device. Due to the immediate spatial proximity, a specific connection line between the suction chamber V and the suction side 12 of the pump 11 is omitted. The passage 9 in the chamber wall 6 leads directly into the cylinder space of the pump 11 which forms the suction side 12. A cut-off valve 18 is arranged in the passage 9 in the depicted embodiment.

With continued reference to FIGS. 5 and 6, to operate the pump 11, a piston rod 16 projects from the suction side of the piston 15 and out of the cylinder 14. A further rod-shaped formation projects from the pressure side of the piston 15, said formation comprising a locking means 19, for example a locking hook, at its exposed end. To operate the pump, the user pushes the piston rod 16 into the cylinder 14 and thus pushes the piston 15 from the suction side 12 of the pump toward the pressure side 13 of the pump, until the locking means 19 locks with an opposite locking means in the cylinder 14. The pump is now tensed and the administering device is ready for administering the product. By placing the opening rim 6' of the suction chamber V on the tissue and then opening the hitherto still closed cut-off valve 18, the product is administered in the manner already outlined above.

Figure 7:
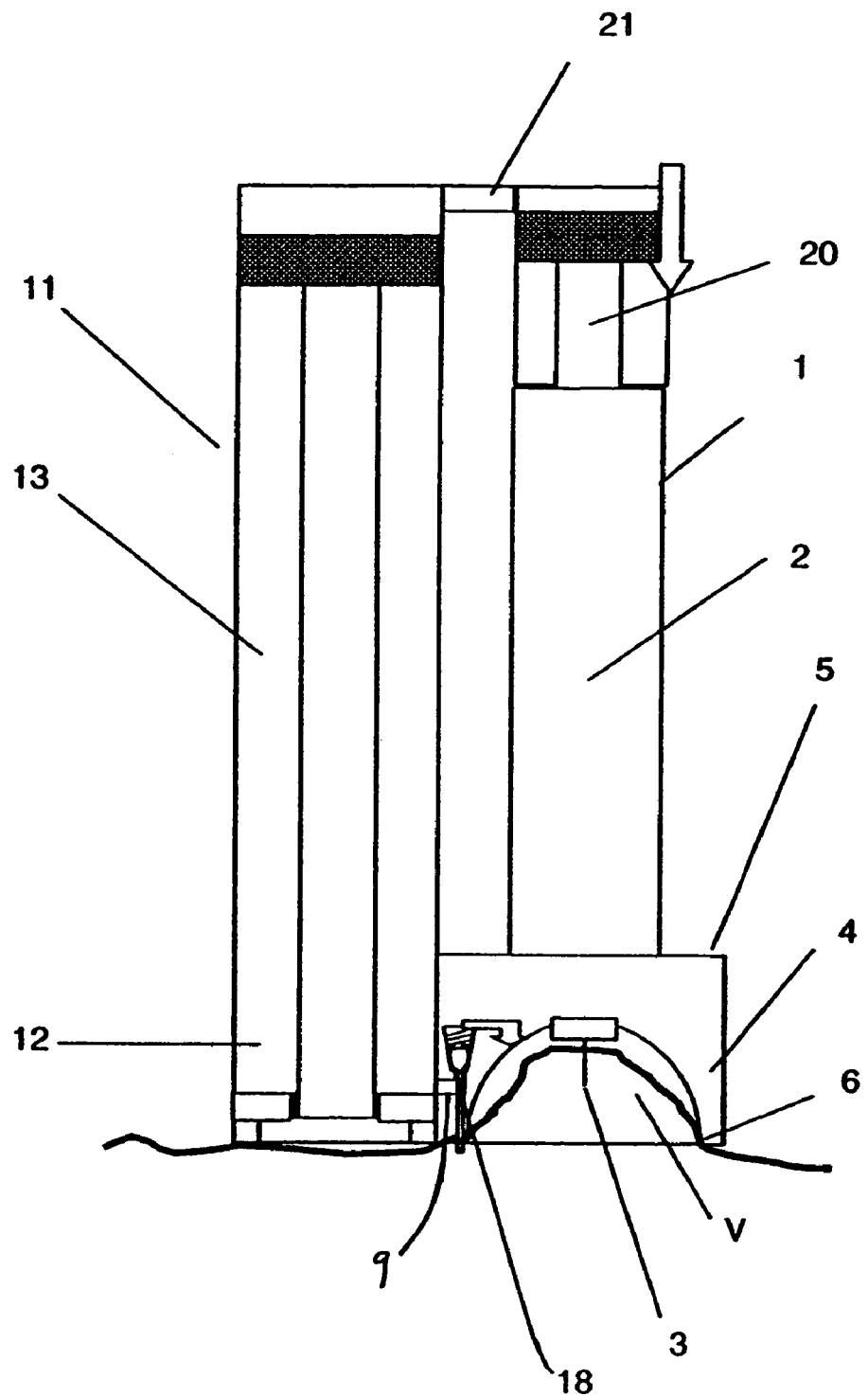
FIG. 7 depicts an administering device comprising a bilaterally acting pump for delivering product.

FIG. 7 shows an administering device comprising a pump 11 which is directly fixed to the casing 1 or integrally formed with it, as in the embodiment in FIGS. 5 and 6. The co-operation between the pump 11 and the suction chamber V corresponds to that of the exemplary embodiments already described. The pump 11 itself is formed like the pump of the embodiment in FIGS. 5 and 6. As opposed to the pump in FIGS. 5 and 6, however, the pump of the embodiment in FIG. 7 is operated as a bilaterally acting pump. The pressure side 13 of the pump 11 is connected to the air-tight sealed inner space of the casing 1 via a pressure line 21. The pressure side 13 acts via the pressure line 21 on the delivery means 20 which in this embodiment is arranged in the sealed inner space of the casing 1.

Under the pressure of the pump, the delivery means 20 acts as a piston, and the casing 1 acts as a cylinder of said piston. Under the influence of the pump pressure, the delivery means 20 is advanced in the proximal direction, slaving a displacing piston accommodated in the product reservoir 2.

Figure 8:
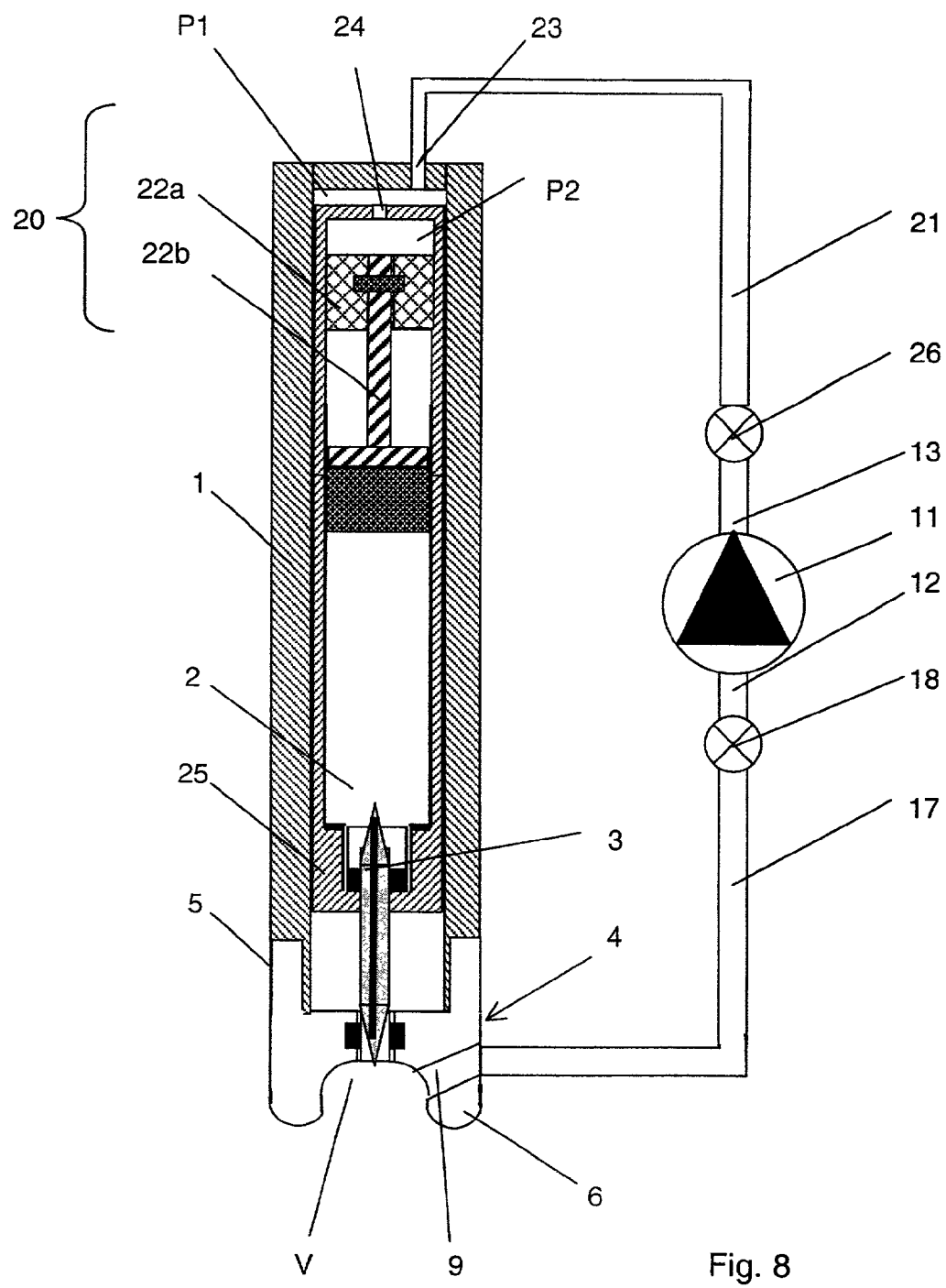
FIG. 8 depicts an administering device comprising a bilaterally acting pump for injecting an injection needle and for delivering product.

The administering device in FIG. 8 is formed by an auto-injection device. The formation of the suction chamber V and the pump and their co-operation again correspond to that of the exemplary embodiments already described. In the exemplary embodiment in FIG. 8, the pressure on the pressure side 13 of the pump is used on the one hand, as in the embodiment in FIG. 7, to operate the delivery means 20, and on the other hand also to move the injection 7 needle 3 relative to the casing 1. In the embodiment in FIG. 8, the injection needle 3 only penetrates the tissue when it is advanced. It would also be conceivable to cause the needle to penetrate more deeply by suctioning the tissue and advancing the needle 3.

The administering device of the embodiment in FIG. 8 can in particular be formed by an auto-injection device such as is described in DE 198 22 031 (run-off control) of the Applicant, the disclosure of which is hereby referred to provide an example of a preferred auto-injection device. The mechanical operation of advancing the needle and the mechanical operation of the delivery means of this pre-described administering device are, however, replaced in accordance with the invention by a pneumatic operation, as shown functionally in FIG. 8. To this end, the pressure side 13 of the pump is connected to the inner space of the casing 1 via a pressure line 21 and a cut-off valve 26 accommodated in it. A carrier means 25, in which the reservoir 2 and the injection needle 3 connected to it are immovably accommodated, forms a piston which is accommodated linearly moveably in the casing I and on the rear side of which the pressure of the pump acts. The delivery means 20 is accommodated within the carrier means 25, said delivery means 20 including a drive member 22a and a driven member 22b which form a spindle drive in a known manner. The delivery means 20 is accommodated in the carrier means 25 linearly moveably relative to the carrier means 25, and forms a further piston. The pressure space P1 between the casing 1 and the carrier means 25 is connected to the pressure space P2 formed behind the delivery means 20 within the carrier means 25 via a passage 24. The adjustment between the passage 23, which leads into the pressure space P1 for the carrier means 25, and the passage 24, which leads into the pressure space P2 for the delivery means 20, is formed such that the run-off control described in DE 198 22 031 for movement of the carrier means 25 and the delivery means 20 is achieved.

In the foregoing description preferred embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

| Reference numerals: | |
|---|---|
| 1 | casing |
| 2 | reservoir |
| 3 | dispensing means, (injection needle, pressure injector, etc.) |
| 4 | suction piece |
| 5 | connection part |
| 6 | chamber wall |
| 7 | passage |
| 8 | seal |
| 9 | passage |
| 10 | tissue |
| 11 | pump |
| 12 | suction side |
| 13 | pressure side |
| 14 | cylinder |
| 15 | piston |
| 16 | piston rod |
| 17 | connection line |
| 18 | valve |
| 19 | locking means |
| 20 | delivery means |
| 21 | pressure line |
| 22a | drive member |
| 22b | driven member |
| 23 | passage |
| 24 | passage |
| 25 | carrier means |
| 26 | valve |

What is claimed is:

1. A device for administering an injectable product from a reservoir, through a dispensing means, and into a tissue of a patient, the device comprising:

a casing for holding the reservoir;

a suction chamber connected to the casing and adapted to abut against the tissue, the dispensing means terminating within the suction chamber;

a piston pump comprising a cylinder, a piston, a piston rod, and a lock, a pressure side being provided on one side of the piston and a suction side being provided on the other side of the piston, wherein the piston rod may be operated to displace the piston within the cylinder to create a state of reduced pressure within the cylinder and, during the use of the device, in the suction chamber, and wherein the lock is adapted to lock the piston in place to maintain the state of reduced pressure in the cylinder;

a passage interconnecting the suction chamber to the reduced pressure; and a cut-off valve located along the passage and adapted to isolate the suction chamber from the reduced pressure, wherein, after abutting the suction chamber against the tissue of the patient, the cut-off valve may be opened, thereby placing the suction chamber and the reduced pressure in the cylinder in fluid communication causing a state of reduced pressure within the suction chamber and bringing the tissue in contact with the dispensing means.

2. The device of claim 1 further comprising a delivery means adapted to cause the injectable product to travel from the reservoir, through the dispensing means, and into the tissue.

3. The device of claim 1 wherein a longitudinal axis of the cylinder runs parallel and adjacent to a longitudinal axis of the casing.

4. The device of claim 1 wherein the lock is located on the piston rod.

5. The device of claim 4 further comprising a lock associated with the cylinder, wherein the lock located on the piston rod and the lock associated with the cylinder are adapted to lock together.

6. The device of claim 5 wherein the dispensing means is a needle.

\* \* \* \* \*